United States Patent [19]

Jirkovsky et al.

[11] 4,035,495

[45] July 12, 1977

[54] PYRROLOBENZOXAZINES, PYRROLOBENZOTHIAZINES AND PROCESS THEREFOR

[75] Inventors: Ivo Jirkovsky, Montreal; Leslie G. Humber, Dollard des Ormeaux, both of Canada

[73] Assignee: Ayerst McKenna and Harrison Ltd., Montreal, Canada

[21] Appl. No.: 548,318

[22] Filed: Feb. 10, 1975

[51] Int. Cl.² .............. A61K 31/54; A61K 31/535; C07D 265/28; C07D 279/16
[52] U.S. Cl. .................... 424/246; 424/248.56; 260/243 R; 260/244 R; 260/247.5 FP
[58] Field of Search ... 260/243 R, 244 R, 247.5 FP; 424/246, 248, 248.56

[56] References Cited
U.S. PATENT DOCUMENTS 3,829,421  8/1974  Irmscher et al. ............... 260/243 R
3,910,901  10/1975  Demerson et al. ............... 260/243

Primary Examiner—John M. Ford
Attorney, Agent, or Firm—Stephen Venetianer

[57] ABSTRACT

4H-Pyrrolo[2,1-c][1,4]benzoxazines and 4H-pyrrolo[2,1-c]-[1,4]benzothiazines characterized by having an alkylamine substituent at position 4 are disclosed. The compounds are characterized further by having an alkyl substituent on the same carbon atom bearing the alkylamine substituent. In addition the compounds may be optionally substituted at positions 1 and 6 to 9. Also disclosed are 4H-pyrrolo-[2,1-c][1,4]benzoxazines and 4H-pyrrolo[2,1-c][1,4]benzothiazines which are dialkylated at position 4 and have a methylamino substituent at position 1. The foregoing compounds possess antihypertensive and central nervous system depressant activity and methods for their preparation and use are described.

30 Claims, No Drawings

PYRROLOBENZOXAZINES, PYRROLOBENZOTHIAZINES AND PROCESS THEREFOR

BACKGROUND OF THE INVENTION a. Field of the Invention

This invention relates to pyrrolobenzoxazines and pyrrolobenzothiazines derivatives. More particularly, this invention relates to heterocycles having a 4-substituted-4H-pyrrolo[2,1-c][1,4]-benzoxazine or a -benzothiazine nucleus, to processes for their preparation, to intermediates for the processes and to methods for using the pyrrolobenzoxazines and pyrrolobenzothiazines.

b. Description of the Prior Art

Interest to date in pyrrolo[2,1-c][1,4]benzoxazine and -benzothiazine derivatives have been exiguous. Only recently has the unsubstituted ring system, 4H-pyrrolo[2,1-c][1,4]benzoxazine, been synthesized, M. Artico, et al., J. Heterocycl. Chem., 8, 283 (1971). The compounds of the present disclosure are distinguished from the latter prior art compound by having substituents at a variety of positions on the nucleus, most notably at position 4 of the 4H-pyrrolo[2,1-c][1,4]benzoxazine and -benzothiazine ring system. Moreover, the synthesis reported by Artico, et al., is not suitable for preparing 4-substituted 4H-pyrrolo[2,1-c][1,4]benzoxazines since it elaborates the carbon atoms at position 4 of the pyrrolobenzoxazine from formaldehyde in a Mannich-type reaction. Prior pharmacologic interest in this class of heterocycles appears to be practically non-existant except for an investigation of certain 1,2,3,3a-tetrahydro-4-H-pyrrolo[2,1-c][1,4]benzoxazines as potential antitumor compounds, M. Artico, et al., 11 Farmaco, Ed. Sci., 24, 285 (1969). The latter compounds are distinguished readily from the compounds of the present invention by being cyclic amides with an additional carbonyl function adjacent to the cyclic oxygen; such carbonyl and amide functions being absent in compounds of the present invention.

Notwithstanding the previous limited interest in pyrrolobenzoxazoles and pyrrolobenzothiazines, we now have found a class of 4H-pyrrolo[2,1-c][1,4]benzoxazines and benzothiazines having useful pharmacologic and therapeutic properties.

SUMMARY OF THE INVENTION

One aspect of this invention includes the compounds of formula 1

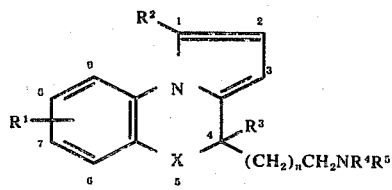

in which $R^1$ is hydrogen, lower alkyl, halogen, lower alkoxy or nitro; $R^2$ is hydrogen, halogen, nitro, lower alkanoyl, trifluoroacetyl or $CH_2NR^4R^5$ in which $R^4$ and $R^5$ are the same or different selected from the group consisting of hydrogen and lower alkyl, or $R^4$ and $R^5$ together with the nitrogen atom to which they are joined form a heterocyclic amine radical selected from the group consisting of 1-pyrrolidinyl, piperidino, morpholino, 1-piperazinyl and 4-(lower alkyl)-1-piperazinyl; $R^3$ is lower alkyl; $R^4$ and $R^5$ are as defined herein; X is oxy or thio; and $n$ is an integer from zero to two.

The acid addition salts of the compounds of formula 1 with pharmaceutically acceptable acids also are included within the scope of this invention.

The compounds of formula 1 are prepared by a process comprising:
condensing a compound of the formula 2

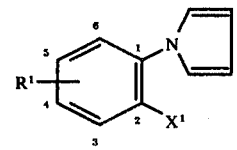

in which $R^1$ is as defined herein and $X^1$ is hydroxy, mercapto, $—S—SO_3—Na$ or $—S—SO_3—K$ with a compound of formula

wherein $R^3$ is a lower alkyl, n is an integer from zero to two and A is selected from the group consisting of:
a. $COOR^6$ in which $R^6$ is hydrogen or lower alkyl,
b. $CONR^4R^5$ in which $R^4$ and $R^5$ are as defined herein,
c. $CH_2OCOR^7$ in which $R^7$ is lower alkyl,
d. $CH_2NR^4COR^8$ in which $R^4$ is as defined herein and $R^8$ is an alkyl containing from one to five carbon atoms, and
e. $CH_2NR^4R^5$ in which $R^4$ and $R^5$ are as defined herein, in the presence of an acid catalyst to obtain the corresponding compound of formula 3

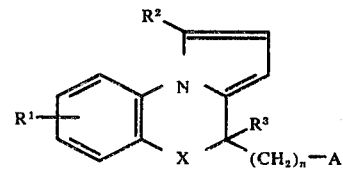

in which $R^1$, $R^3$, X, n and A are as defined hereinabove and $R^2$ is hydrogen; followed, when said compound of formula 3 is different from said compound of formula 1, by transformation of said compound of formula 3 to said compound of formula 1 by methods described herein.

More specifically, the transformation of said compound of formula 3 to said compound of formula 1 comprises:

a. when A of said compound of formula 3 is $COOR^6$ as defined above, hydrolyzing said compound of formula 3 in which $R^6$ is lower alkyl to obtain the corresponding acid (3; A = $COOR^6$ in which $R^6$ is hydrogen), subjecting the acid, obtained from either the condensation or hydrolysis reaction, to amidation with an appropriate amine of formula $NHR^4R^5$ in which $R^4$ and $R^5$ are as defined herein to give the corresponding amide (3; A = $CONR^4R^5$), and reducing the amide with a suitable complex metal hydride;

b. when A of said compound of formula 3 is $CONR^4R^5$, reducing said compound of formula 3 with a complex metal hydride;

c. when A of said compound of formula 3 is $CH_2O-COR^7$, hydrolyzing said compound of formula 3 with a suitable alkali to give the corresponding primary alcohol (3; A=CH$_2$OH), reacting said alcohol with a mesylating or tosylating agent and reacting the resulting respective mesylated or tosylated intermediate with an amide of formula NHR$^4$R$^5$ in which R$^4$ and R$^5$ are as defined herein; or d. when A of said compound of formula 3 is CH$_2$NR$^4$COR$^8$, reducing said compound of formula 3 with a complex metal hydride;

to obtain the corresponding compound of formula 1 in which R$^2$ is hydrogen.

Thereafter and if desired, the corresponding compound of formula 1 in which R$^2$ is halogen, nitro, lower alkanoyl or trifluoracetyl obtained by reacting the compound of formula 1 in which R$^2$ is hydrogen with the appropriate nucleophilic reagent or by reacting the appropriate compound of formula 3 in which R$^2$ is hydrogen with the appropriate nucleophilic reagent to obtain the corresponding compound of formula 3 in which R$^2$ is halogen, nitro, lower alkanoyl or trifluoroacetyl and then transforming the latter compound to the corresponding compound of formula 1 by methods described herein. The corresponding compound of formula 1 in which R$^2$ is CH$_2$NR$^4$R$^5$ wherein R$^4$ and R$^5$ are as defined herein is obtained by reacting the corresponding compound of formula 1 in which R$^2$ is hydrogen with formaldehyde and an amine of formula NHR$^4$R$^5$ according to the conditions of the Mannich reaction to obtain the desired compound of formula 1 directly or by reacting the corresponding compound of formula 3 in which R$^2$ is hydrogen with formaldehyde and the amine under the conditions of the Mannich reaction to obtain the corresponding compound of formula 3 in which R$^2$ is CH$_2$NR$^4$R$^5$ wherein R$^4$ and R$^5$ are as defined herein and then transforming the latter compound to the corresponding compound of formula 1 by methods described herein.

Again thereafter, and if desired the preceding compounds of formula 1 are converted to their corresponding acid addition salts.

Another aspect of this invention includes the compounds of formula 4

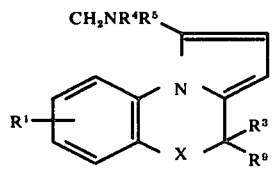

in which R$^1$, R$^3$, R$^4$, R$^5$ and X are as defined herein and R$^9$ is lower alkyl, and the acid addition salts thereof with pharmaceutically acceptable acids.

The compounds of formula 4 are prepared by a process comprising: reacting the compound of formula 2, as described herein, with a ketone of formula

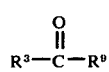

in which R$^3$ and R$^9$ are as described herein, in the presence of an acid catalyst to obtain the compound of formula 5

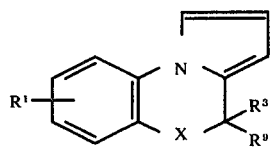

in which R$^1$, R$^3$, R$^9$ and X are as defined herein, and reacting the last-named compound with formaldehyde and an amine of formula NHR$^4$R$^5$ in which R$^4$ and R$^5$ are as described herein according to the conditions of the Mannich reaction to obtain the corresponding compound of formula 4, and if desired forming the acid addition salt thereof with pharmaceutically acceptable acid.

The compounds of formula 1 and 4 and their pharmaceutically acceptable acid addition salts exhibit antihypertensive and central nervous system depressant activities.

In still another aspect of this invention the intermediate compounds of formula 3 in which A is COOH and X is oxy exhibit antifungal activity.

DETAILED DESCRIPTION OF THE INVENTION

The term "lower alkyl" as used herein contemplates straight chain alkyl radicals containing from one to six carbon atoms and branched chain alkyl radicals containing three to four carbon atoms and includes methyl, ethyl, propyl, isopropyl, butyl, isobutyl, pentyl, hexyl and the like.

The term "lower alkoxy" as used herein contemplates both straight and branched chain alkoxy radicals containing from one to four carbon atoms and includes methoxy, ethoxy, isopropoxy, butoxy and the like.

The term "lower alkanoyl" is used herein contemplates both straight and branched chain alkanoyl radicals containing from two to six carbon atoms and includes acetyl, propionyl, isobutyryl, hexanoyl and the like.

The terms "halogen" and "halo" as used herein contemplate halogens and include flourine, chlorine, bromine and iodine.

The acid addition salts of the pyrrolobenzoxazines and pyrrolobenzothiazines of formulae 1 and 4 are prepared by reacting the base form of the pyrrolobenzoxazine or pyrrolobenzothiazine with substantially one to four equivalents, depending on the number of basic nitrogens in the compound, or preferably with an excess of the appropriate acid in an organic solvent, for example, ether or an ethanol-ether mixture. These salts, when administered to mammals, possess the same pharmacologic activities as the corresponding bases.

For many purposes it is preferable to administer the salts rather than the base compounds. Among the acid addition salts suitable for this purpose are salts such as the sulfate, phosphate, lactate, tartrate, maleate, citrate, hydrobromide and hydrochloride. Both the base compounds and the salts have the distinct advantage of possessing a relatively low order of toxicity.

Also included in this invention are the stereochemical isomers of the compounds of formula 1 which result from asymmetric centers, contained therein. These isomeric forms may be prepared by chemical methods and are purified readily by crystallization or chromatography.

Individual optical isomers, which might be separated by fractional crystallization of the diastereoisomeric salts formed thereof, for instance, with d- or l-tartaric acid or D-(+)-α-bromocamphor sulfonic acid, are also included.

ANTIHYPERTENSIVE ACTIVITY

The antihypertensive effect of the compounds of formulae 1 and 4 and their acid addition salts is demonstrated in standard tests, for example, in tests conducted in the spontaneously hypertensive rat (SHR) such as described by R. Tabei, et al., Clin. Pharmacol. Therap., 11, 269 (1970) or J. Vavra, et al., Can. J. Physiol. Pharmacol., 51, 727 (1973). More specifically exemplified, a testing method such as described in the latter publication shows that 4-[2-(dimethylamino)ethyl]-4-methyl-4H-pyrrolo[2,1-c][1,4]benzoxazine hydrochloride (see Example 42) and 1-[(dimethylamino)methyl]-4,4-dimethyl-4H-pyrrolo[2,1-c][1,4]-benzoxazine hydrochloride (see Example 79) cause a notable blood pressure decrease in the SHR at about 4 hours after a dose of 25 - 50mg/kg/perorally.

When the compounds of formulae 1 and 4 of this invention are used as antihypertensive agents in warm-blooded animals, e.g. rats, dogs and mice, they are used alone or in combination with pharmacologically acceptable carriers, the proportion of which is determined by the solubility and chemical nature of the compound, chosen route of administration and standard biological practice. For example, they are administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the pyrrolobenzoxazines and pyrrolobenzothiazines will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstance is reached. In general, the compounds of this invention are most desirably administered at a concentration level that will generally afford effective results without causing any harmful or deleterious side effects. The effective antihypertensive amount of the compounds usually ranges from about 1.0 mg to about 500 mg per kilo per day, although as aforementioned variations will occur. However, a dosage level that is in the range of from about 10 mg to about 100 mg per kilo per day is employed most desirably in order to achieve effective results.

The compounds of formulae 1 and 4 also exhibit central nervous system (CNS) depressant activity. The useful CNS depressant activity is demonstrated in standard pharmacologic test, for example, the tests described by R. A. Turner in "Screening Methods in Pharmacology," Academic Press, New York and London, 1965, pp 69 - 99.

When the compounds of formulae 1 and 4 are used as CNS depressants they may be formulated and administered in the same manner as described hereinbefore for their use as antihypertensive agents.

PROCESSES

The starting materials for the process for preparing the compounds of formula 1 are the compounds of the formula 2 and the ketonic compound of formula

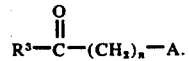

The compounds of formula 2 in which $X^1$ is hydroxy and $R^1$ is as defined herein are prepared readily by condensation of the appropriate 0-aminophenol with 2,5-dimethoxytetrahydrofuran according to a procedure similar to that reported by Artico (1971), cited above, for making 1-(0-hydroxyphenol)pyrrole. The requisite 0-aminophenols are known or are readily prepared by known methods, for instance by the reduction of the corresponding 0-nitrophenols see "Chemistry of Carbon Compound", E. H. Rodd, Ed., Vol. 3A, Elsevier Publishing Co., Amsterdam, 1954, pp 449 - 460.

The compounds of formula 2, in which $X^1$ is —SH, —S—SO$_3$—Na, or —S—SO$_3$—K and $R^1$ is as defined herein are obtained by the following process:

The corresponding 0,0'-diamino-diphenylsulfides of the formula

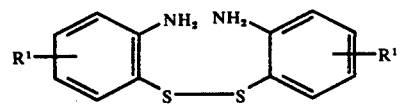

are condensed with 2,5-dimethoxytetrahydrofuran as described herein, and the resultant 0,0'-dithiobis(1-phenylpyrroles) are reduced with lithium aluminum hydride to obtain the compounds of formula 2, in which X' is mercapto. The requisite 0,0'-diamino-diphenylsulfides are readily prepared by air-oxidation of the corresponding 0-aminothiophenols, see A. W. Hofmann, Chem. Ber., 12, 2363. Treatment of the intermediate 0,0'-diamino-diphenylsulfides with sulphurous acid according to German Patent, D.R.P. 120504 [Beilsein, Vol XIII, 4th Ed., p. 400 (1930)] yields the S-(0-aminophenyl-thiosulfuric acids which are condensed with 2,5-dimethoxytetrahydrofuran to afford the compounds of formula 2 in which X' is —S—SO$_3$H. Finally, the latter compounds are converted into the corresponding sodium or potassium salts (X' = —S—SO$_3$-Na or —S—SO$_3$-K).

The starting materials of formula

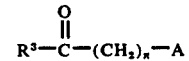

are described below with reference to their specific use in the present process.

The first step of the process for preparing compounds of formula 1 is the condensation of the compound of formula 2 with the compound of formula

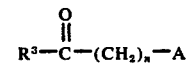

to give the corresponding compound of formula 3.

When practising the condensation, an inert organic solvent is generally used as a reaction medium. Any solvent inert to the reaction conditions may be used. Suitable solvents include benzene, toluene, diethyl ether, dioxan, tetrahydrofuran, methylene dichloride, carbon tetrachloride and the like. Benzene and tetrahydrofuran are especially convenient and practical for this use. However, note that the solvent may be omitted without detrimental effects on the reaction if the reactants are heated to a melt with stirring.

A variety of suitable acid catalysts may be used for this condensation, for example, the type of catalyst used in a Friedel-Crafts reaction, i.e., p-toluenesulfonic acid, aluminum chloride, phosphorus pentoxide, zinc chloride, hydrochloric acid, perchloric acid, trifluoroacetic acid, sulfuric acid, and polyphosphoric acid and the like. See also the list of acid catalysts described by G. A. Olah in "Friedel-Crafts and Related Reactions," Vol. 1, G. A. Olah, Ed., Interscience Publishers, New York, N.Y., 1963, pp 201 – 366, which includes other suitable proton and Lewis acids. p-Toluenesulfonic acid, polyphosphoric acid acetic acid are included among the preferred acid catalysts. The amount of acid catalyst used is not especially critical and may range from 0.01 molar equivalents to 100 molar equivalents with respect to the starting material of formula 2. A range of from 0.1 to 10 molar equivalents is generally preferred; however, note that the amount of acid catalyst should be in excess of one molar equivalent with respect to the compound of formula

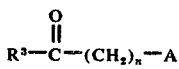

when A is $CH_2NR^4R^5$ as defined herein.

The time of the reaction may range from 10 minutes to 60 hours, with the preferred range being from one-half to 24 hours. The temperature of the reaction may range from 20° C to 160° C.

A more detailed description of the preparation of the compounds of formula 3 and a description of their subsequent conversion of the compounds of formula 1 are disclosed below. For convenience these descriptions are categorized into sections according to the group selected for A of the starting material of formula

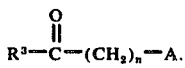

A. PREPARATION AND CONVERSION OF INTERMEDIATES OF FORMULA 3 (A = COOR⁶)

Intermediates of formula 3 in which A is $COOR^6$ wherein $R^6$ is hydrogen or lower alkyl are readily obtained by the above condensation using ketoacids or ketoesters of formula

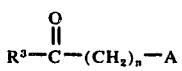

in which $R^3$ and $n$ are as defined above and A is $COOR^6$ as defined above together with the starting material of formula 2.

Generally comparable yields of product are obtained in this process when either the ketoacid or the corresponding ketoester is used. However, in the case where it is desired to prepare an acid compound of formula 3 in which A is COOH and $n$ is the integer one (i.e., an acetic acid intermediate of formula 3), it is preferable to condense the appropriate β-ketoester rather than the corresponding β-ketoacid and then hydrolyze the resulting ester product to give the desired acid compound.

Moreover, in the general practise of this invention it is often more convenient to prepare the acid compounds of formula 3 by using the ketoester instead of the ketoacid in this process and hydrolyze the resulting ester product to the desired acid, the reason being simply that the ketoesters are generally more readily available either commercially or by synthesis.

The hydrolysis of compounds of formula 3 in which A is $COOR^6$ wherein $R^6$ is lower alkyl, i.e. ester intermediates of formula 3, to their corresponding acids of formula 3, is effected by treatment with a suitable alkali, for example, potassium hydroxide or sodium carbonate, in aqueous methanol or aqueous ethanol or by treatment with lithium iodide in a suitable organic solvent, for example, collidine, see L. F. Fieser and M. Fieser, "Reagents for Organic Synthesis," John Wiley and Sons, Inc., New York, 1967, pp. 615 – 617.

The α-, β-, γ- and δ-ketoacids and -ketoesters of formula

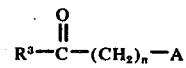

are either known, for example, eithyl pyruvate, levulinic acid, ethyl α,α-dimethylacetoacetate, and β,β-dimethyllevulic acid, or they may be prepared by known methods described in general organic chemistry textbooks. For example, a comprehensive review of the properties and preparation of such α-, β-, γ- and δ-ketoacids and -ketoesters may be found in "Rodd's Chemistry of the Carbon Compounds", S. Coffey, Ed., Vol. 1d, 2nd ed., Elsevier Publishing Co., Amsterdam, 1965, pp. 226 – 274.

Thereafter these intermediate acids and esters of formula 3 are converted by amidation followed by reduction to compounds of formula 1 in which $R^1$, $R^3$, $R^4$, $R^5$, X and $n$ are as defined above and $R^2$ is hydrogen.

More specifically, in the case where the acid intermediate of formula 3 is employed, said acid is subjected to amidation by treatment with a lower alkyl chloroformate, preferably ethyl chloroformate, in the presence of triethylamine, affording the corresponding mixed anhydride, which is converted by treatment with the appropriate amine of formula $HNR^4R^5$ in which $R^4$ and $R^5$ are as defined above, for example, ammonia, methylamine or dimethylamine, to yeild the corresponding amide of formula 3 in which A is $CONR^4R^5$.

Alternatively, the latter amides are also obtained by treating the ester intermediates of formula 3 with the appropriate amine according to known amidation methods, for example, see A. L. F. Beckwith in "The Chemistry of Amides," J. Zalicky, Ed., Interscience Publishers, New York, 1970, pp. 96 – 105.

Thereafter, the amides so obtained are reduced with a suitable complex metal hydride to yield the desired compound of formula 1. Examples of suitable complex metal hydrides are lithium aluminum hydride, lithium alumium hydride-aluminum chloride, aluminum hydride-aluminum chloride, diborane and sodium borohydridealuminum chloride. Lithium aluminum hydride is preferred.

A modification relating to the preceding general reduction of the above amides of formula 3 in which A is $CONR^4R^5$ wherein $R^4$ and $R^5$ are as defined above is applicable to the reduction of the tertiary, secondary and primary amides, described herein, and is a preferred modification for the reduction of the latter two. In practising this modification, the aforementioned amide of formula 3 is treated with triethyloxonium fluoroborate or dimethyl sulfate, see H. Bredereck, et al., Chem. Ber., 98, 2754 (1965), in an inert solvent, for example, methylene dichloride, whereby the corresponding iminoether fluoroborate or methyl sulfate salt is obtained, respectively. Subsequent reduction of the salt thus obtained with a complex metal hydride, similar to the reduction described previously for the amides, yields the corresponding compounds of formula 1. Alternatively, the above fluoroborate or methyl sulfate salt derived from a secondary or primary amide is decomposed by base treatment, for example, with 10% sodium hydride or triethylamine, to give the corresponding iminoether which is then reduced in a like manner to the desired compound of formula 1.

B. PREPARATION AND CONVERSION OF INTERMEDIATE OF FORMULA 3 (A = CONR⁴R⁵)

The intermediates of formula 3 in which A is $CONR^4R^5$ wherein $R^4$ and $R^5$ are as described above, see also section (a), are also obtained directly by utilizing the appropriate starting materials of formula 2 and α-, β-, γ, or δ-ketoamides of formula

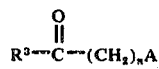

in which $R^3$ and $n$ are as defined above and A is $CONR^4R^5$ in which $R^4$ and $R^5$ are as defined above. The ketoamides required for this condensation are either known, for example, pyruvamide or α,α-dimethylacetoacetamide, or they may be prepared by known methods, for instance, see "Rodd's Chemistry of the Carbon Compounds", cited above, Vol. 1d, pp. 226 – 274.

Thereafter these amides are converted by the reduction process, described above, to the compounds of formula 1 in which $R^1$, $R^3$, $R^4$, $R^5$, X and $n$ are as defined above and $R^2$ is hydrogen.

C. PREPARATION AND CONVERSION OF INTERMEDIATES OF FORMULA 3 (A = CH₂OCOR⁷)

Intermediates of formula 3 in which A is $CH_2OCOR^7$ wherein $R^7$ is lower alkyl are obtained when a starting material of formula 2 is condensed with a ketoalcohol lower alkanoic acid ester of formula $R^3CO(CH_2)_n$-A in which $R^3$ and $n$ are as defined above and A is $CH_2OCOR^7$ in which $R^7$ is as defined above in the presence of a suitable acid catalyst according to the condensation conditions described above. The ketoalcohol lower alkyl esters are either known, for example, acetonyl acetate or 5-acetoxypentan-2-one, or may be prepared by knwon methods, for instance, see "Rodd's Chemistry of the Carbon Compounds", cited above Vol. 1d, pp 49 – 54.

These intermediates of formula 3 are utilized for the preparation of compounds of formula 1 of this invention in the following manner: The intermediate is hydrolyzed with an aqueous alcoholic solution of a suitable alkali, for example, sodium or potassium hydroxide in aqueous methanol, to afford the corresponding primary alcohol. It should be noted also that the primary alcohol is obtained directly by the reduction of the appropriate intermediate acids or intermediate esters of formula 3, described herein in section (a), using a suitable complex metal hydride as described therein.

The above corresponding alcohol next is converted to a reactive intermediate such as the corresponding mesylate or tosylate, which is then reacted with two or more molar equivalents of an amine of formula $HNR^4R^5$ in which $R^4$ and $R^5$ are as defined above. Preferably this reaction is performed in a suitable inert solvent, for example, tetrahydrofuran, at the boiling point of the reaction mixture for a period of eight to 24 hours.

If desired the compounds of formula 1 in which both $R^4$ and $R^5$ are hydrogen may be further N-alkylated on the nitrogen of the primary amine with the appropriate lower alkyl halide to the corresponding compounds of formula 1 in which $R^4$ is hydrogen or lower alkyl and $R^5$ is lower alkyl (i.e., secondary or tertiary amines), In this case depending on the particular derivative desired the N-alkylation may be effected with one or two moles of the alkyl halide to give respectively the secondary ($R^4$ = H and $R^5$ = lower alkyl) or tertiary amine ($R^4$ = $R^5$ = lower alkyl). On the other hand the N-alkylation may be effected in two steps introducing a different alkyl group each time to afford the corresponding tertiary amine in which $R^4$ and $R^5$ are different lower alkyls. When it is desired to prepare the above tertiary amine compounds in which $R^4$ or $R^5$ are either or both methyl, an alternative alkylation method comprises reacting the appropriate corresponding primary or secondary amine with an aqueous mixture of a substantial excess of formaldehyde and formic acid according to the conditions of the Eschweiler-Clarke reaction, see M. L. Moore, Organic Reactions, 5, 301 (1949), whereby N-methylation is effected.

D. PREPARATION AND CONVERSION OF INTERMEDIATES OF FORMULA 3 (A = CH₂NR⁴COR⁸)

Intermediates of formula 3 in which A is $CH_2NR^4COR^8$ wherein $R^4$ is lower alkyl and $R^8$ is an alkyl containing one to five carbon atoms are readily obtained by the above condensation by using ketoamides of formula

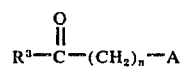

in which $R^3$ and $n$ are as defined above and A is $CH_2NR^4COR^8$ wherein $R^4$ and $R^8$ are as defined above together with the appropriate starting material of formula 2.

The ketoamides used herein are either known, for example, formamidoacetone [see A. Treibs and W. Sutter, Chem. Ber., 84, 96 (1951) and R. H. Wiley and O.H. Borum, J. Amer. Chem. Socl, 70, 2005 (1948)] or may be prepared by known procedures, for example, see "Methoden der Organischen Chemie," cited above, Vol. XI/I, 1957, especially pp. 58 – 62, 285 – 289 land 508 – 509, and F. F. Blicke, Organic Reactions, 1, 303 (1942).

Thereafter, reduction with a complex metal hydride, described in section (a), converts the instant intermediates to compounds of formula 1 in which $R^1$, $R^3$, $R^4$, $R^5$, X and $n$ are as defined above and $R^2$ is hydrogen.

E. PREPARATION OF COMPOUNDS OF FORMULA 3 (A = CH₂NR⁴R⁵) ≡ Compounds of Formula 1

The starting materials of formula 2 in which R¹ is as defined above are condensed in the presence of an acid catalyst with an aminoketone of formula R³CO—(CH₂)ₙ-A in which R³ and n are as defined above and A is CH₂NR⁴R⁵ wherein R⁴ and R⁵ are as defined above to give directly the compounds of formula 1.

The requisite aminoketones for this reaction are either known, for example, 1-dimethylamino-3-butane, 1-methylamino-3-pentanone, see F. F. Blicke, cited above, or they may be prepared by known procedures, for example, see "Methoden der Organic Chemie", cited above, Vol. XI/I, 1957, pp. 58 – 62, 285 – 289 and 508 – 509.

In practising this present condensation it is generally advantageous to utilize substantially equimolar amounts of the starting material of formula 2 and the aminoketone in the presence of an acid catalyst. In this particular condensation the amount of the aforementioned acid catalyst to employ ranges generally from about 1.01 to 100 molar equivalents with respect to the amount of aminoketone reactant, a range of from 1.05 to 10 molar equivalents being preferred. Optionally, one may employ the acid addition salts of the aforementioned aminoketones, for example the hydrochloride or the sulfate salt. In this case the amount of acid catalyst, for example, p-toluenesulfonic acid, may range from 0.01 to 100 molar equivalents. The reaction is performed conveniently and advantageously in an inert organic solvent, for example, toluene, 0-xylene or isobutyl ether. Reaction time and temperature depends on the particular reactants employed and may be varied. The most convenient reaction time is from ½ to 48 hours, preferably ½ to 8 hours, and reaction temperatures from 20° to 100° C, preferably 40° to 80° C.

For the preparation of the compounds of formula 1 in which R² is halogen, nitro, lower alkanoyl or trifluoroacetyl, the appropriate compound of formula 1 or 3, for example the compound of formula 3 in which A is COOR⁶ in which R⁶ is as defined above or CONR⁴R⁵ in which R⁴ and R⁵ are as defined above, is reacted with a nucleophilic reagent capable of introducing the desired substituent on the pyrrolobenzoxazine or pyrrolobenzothiazine. The choice of the reagent depends on the substituent to be introduced. Generally, any of the nucleophilic reagents known to be effective for introducing a substituent on an aromaic ring are useful; see for example, L. F. Feiser and M. Feiser, "Advanced Organic Chemistry," Reinhold Publishing Corp., New York, N.Y., 1961, pp. 620 – 638. Preferred reagents include sulfuryl chloride for introducing the chlorine substituent, sulfuryl bromide for a bromine substituent, a lower alkanoic anhydride for the trifluoroacetyl substituent. For the nitro substituent convenient conditions are those using 90% nitric acid in acetic anhydride at −70° to 20° C for 30 to 180 minutes. In this manner, the compound of formula 1 in which R² is hydrogen affords the corresponding compound of formula 1 on which R² is halogen, nitro, lower alkanoyl or trifluoromethyl and the compound of formula 3 in which R² is hydrogen affords the corresponding compounds of formula 3 in which R² is halogen, nitro, lower alkanoyl or trifluoromethyl. Thereafter the latter compound of formula 3 is transformed to the corresponding compound of formula 1 in the manner described above for such transformations.

For the preparation of the compounds of formula 1 in which R² is CH₂NR⁴R⁵ as defined herein, the appropriate compound of formulae 1 or 3, for example the compound of formula 3 in which A is COOR⁶ in which R⁶ is as defined above or CONR⁴R⁵ in which R⁴ and R⁵ are as defined above, is reacted with formaldehyde and an amine of formula NHR⁴R⁵ in which R⁴ and R⁵ are as defined above according to the conditions of the Mannich reaction. In this manner the compound of formula 1 in which R² is hydrogen affords the corresponding compound of formula 1 in which R² is CH₂NR⁴R⁵ wherein R⁴ and R⁵ are as defined herein and the compound of formula 3 in which R² is hydrogen affords the corresponding compound of formula 3 in which R² is CH₂NR⁴R⁵ wherein R⁴ and R⁵ are as defined herein. Convenient conditions for effecting the above Mannich reaction are described hereinafter. However, it should be noted that when R¹ of the aforementioned compound of formula 1 and 3 is a 7-alkyl or 7-halo substituent, the above-mentioned Mannich type reaction proceeds very slowly.

A process for the preparation of the compounds of formula 4 in which R¹, R³, R⁴, R⁵ and R⁹ are as defined hereinabove comprises condensing the appropriate aforementioned compound of formula 2 with a ketone of formula

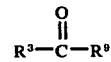

in which R³ and R⁹ are as defined hereinabove, in the presence of an acid catalyst to obtain the corresponding pyrrolobenzoxazine or pyrrolobenzothiazine of formula 5. The same conditions and acid catalysts described herein for the condensation of the compound of formula 2 with the compound of formula

are used for the present condensation.

However, it should be noted that a side reaction also occurs during the latter condensation. The by-product formed as a result of the side reaction is represented by formula 6

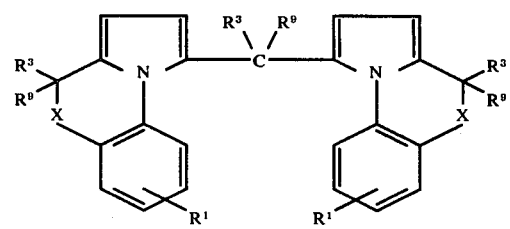

in which R¹, R³, R⁹ and X are as defined hereinabove.

The formation of this by-product can be reduced substantially by mixing first the compound of formula 2 and the acid catalyst in one of the above inert solvents, for example, benzene or toluene, and heating the mixture for 10 to 60 minutes at 40° to 100° C or at the boiling point of the solvent. Thereafter, the ketone of formula

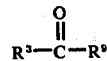

is added to the mixture and the condensation is allowed to proceed in the manner described previously. The by-product and the compound of formula 5 are separated and purified readily by conventional techniques. Extraction and chromatography are preferred techniques for this purpose.

The requisite ketones of formula

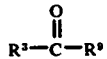

are known, for example, acetone and methyl ethyl ketone, or are prepared by known methods; for example, see P. Karrer, "Organic Chemistry", 4th Eng. Ed., Elsevier Publishing Co., New York, N.Y., 1950, pp. 172 – 180.

Returning now to the aforementioned compound of formula 5, this compound is transformed into the corresponding pyrrolobenzoxazine or pyrrolobenzothiazine of formula 4 by reacting the compound of formula 5 with an excess formaldehyde and the appropriate amine of formula $HNR^4R^5$ as defined above according to the conditions of the Mannich reaction; see for example F. F. Blicke, cited above. Convenient conditions for effecting this reaction include the employment of 1.5 to 10 molar equivalents of formaldehyde and the appropriate amine in an inert solvent such as ethanol, acetic acid or tetrahydrofuran at 30° to 65° C for ½ to 5 days.

As mentioned previously, the intermediate compound of formula 3 in which A is COOH and X is oxy exhibit antifungal activity. More particularly, the useful antifungal activity the latter compounds of formula 3 against a number of pathogenic fungi, for example, *Candida alibicans, Microsporum gypseum* and *Trichophyton granulosum*, is demonstrable in standard tests used for this purpose, for example, in the test described in "Antiseptics, Disinfectants, Fungicides and Sterilization," G. F. Reddish, Ed., 2nd ed., Lea and Febiger, Philadelphia, 1957 or by D.C. Grove and W. A. Randall in "Assay Methods of Antibiotics", Med. Encycl. Inc., New York 1955. As antifungal agents the aforementioned compound of formula 3 are most effective when used topically, and are preferably employed in the form of solutions, creams, or lotions in pharmaceutically acceptable vehicles containing from 0.1–10 percent of the active ingredient, such solutions, creams, or lotions to be applied to infected areas of the skin from one to three times daily.

The following examples illustrate further this invention.

EXAMPLE 1

N-(2-Hydroxyphenyl)pyrrole (2, $R^1 = H$ and $X^1 = OH$)

A mixture of 2,5-dimethoxytetrahydrofuran (39.6 g), o-aminophenol (36 g), dioxane (300 ml), and glacial acetic acid (180 ml) are heated under reflux for 4 hr. The solvents are removed and the residue distributed between ethyl acetate and 5% $NaHCO_3$. The organic phase is washed with water, dried ($MgSO_4$), filtered, and evaporated. The dark oily residue is subjected to chromatography on 2 kg of silica and eluted with chloroform to afford an oil. After being covered with hexane and stored for several days, the oil solidifies giving the title compound, m.p. 52° – 54° C. (Reported m.p. by Artico, et al., cited above, 45° – 47° C).

In the same manner but replacing o-aminophenol with appropriately substituted o-aminophenols, other hydroxyphenylpyrroles of formula 2 are obtained. For example, replacement of o-aminophenol with an equivalent amount of 2-amino-5-chlorophenol gives N-(5-chloro-2-hydroxyphenyl)pyrrole, $\nu_{max}^{CHCl_3}$ 1,500, 1,345, 1,070, 1,020 $cm^{-1}$.

Similarly, replacement with 2-amino-4-nitrophenol gives N-(2-hydroxy-5-nitrophenyl)pyrrole, m.p. 80° – 81° C.

EXAMPLE 2

4-Methyl-4H-pyrrolo[2,1-c][1,4]benzoxazine-4-acetic acid (3; $R^1$ and $R^2 = H, R^3 = CH_3$, X = O, n = 1 and A = COOH)

A solution of the compound of formula 2, N-(2-hydroxyphenyl)pyrrole (5 g), described in Example 1, ethyl acetoacetate (4.3 g) and p-toluenesulfonic acid (0.5 g) in benzene (1,500 ml) is stirred and heated at reflux with a Dean-Stark water trap for 3 hr. Ethyl acetoacetate (1.0 g) is added and the reaction mixture kept under the refluxing condition overnight. After being cooled, the mixture is washed with a 5% solution of sodium bicarbonate and then water. The benzene solution is dried ($MgSO_4$), filtered and evaporated. The crude product is purified by chromatography on a column of silica gel. Elution with chloroform gives 4-methyl-4H-pyrrolo[2,1-c][1,4]benzoxazine-4-acetic acid ethyl ester (3; $R^1$ and $R^2 = H, R^3 = CH_3$, n = 1, X = O and A = $COOC_2H_5$), $\nu_{max}^{CHCl_3}$ 1,725, 1,600, 1,505, 1,345, 1,080, 1,031 $cm^{-1}$.

The latter ester (13.5 g) is mixed with 300 ml of methanol and 15 ml of 50% NaOH. The reaction mixture is heated at reflux for 3 hr. The methanol is removed under reduced pressure and the aqueous solution extracted with ether. The clear solution of the sodium salt is acidified with concentrated HCl and extracted exhaustively with chloroform. The chloroform extract is washed with water, dried ($MgSO_4$), filtered, and evaporated. The residue is crystallized from ether-hexane, to give the title compound, m.p. 121° – 122° $\nu_{max}^{CHCl_3}$ 3,000, 1,700 $cm^{-1}$.

In the same manner but replacing N-(2-hydroxyphenyl)pyrrole with an equivalent amount of N-(5-chloro-2-hydroxyphenyl)pyrrole, described in Example 1, 8-chloro-4-methyl-4H-pyrrolo[2,1-c][1,4]-benzoxazine-4-acetic acid, $\nu_{max}^{CHCl_3}$ 2,900 – 2,500, 1,728, 1,498, 1,445 $cm^{-1}$, is obtained via the intermediate ester, 8-chloro-4-methyl-4H-, pyrrolo[2,1-c][1,4]benzoxazine-4-acetic acid ethyl ester, $\nu_{max}^{CHCl_3}$ 1,732 $cm^{-1}$.

In the same manner but replacing N-(2-hydroxyphenyl)-pyrrole and ethyl acetoacetate with an equivalent amount of N-(2-hydroxy-5-nitrophenyl)pyrrole, described in Example 1, and methyl acetoacetate, respectively, 4-methyl-8-nitro-4H-pyrrolo[2,1-c][1,4]benzoxazine-4-acetic acid, nmr ($CDCl_3$) δ 1.89 (s, 3H), 6.14 (2xd, J = 3.5 and 1.5Hz, 1H), via the intermediate ester, 4-methyl-8-nitro-4H-pyrrolo[2,1-c][1,4]benzoxazine-4-acetic acid methyl ester, m.p. 132° – 133° C, $_{max}^{CHCl_3}$ 1,730 $cm^{-1}$.

EXAMPLE 3

4-Methyl-4H-pyrrolo[2,1-c][1,4]benzoxazine-4-carboxylic acid (3; $R^1$ and $R^2$ = H, $R^3$ = $CH_3$, X = 0, n = 0 and A = COOH)

A solution of the compound of formula 2, N-(2-hydroxyphenyl)pyrrole (18 g), described in Example 1, ethyl pyruvate (13 g) and p-toluenesulfonic acid (1.8 g) in benzene (1.2 l) is stirred and heated at reflux with a Dean-Stark water trap for 30 min. The reaction mixture is allowed to cool and stand at room temperature for 18 hr. The mixture is filtered and the filtrate is washed with 5% $NaHCO_3$, water, saturated brine solution, and then dried ($MgSO_4$). The solvent is evaporated and the remaining material is adsorbed on a silica gel column. Elution with chloroform gives 4-methyl-4H-pyrrolo[2,1-c][1,4]benzoxazine-4-carboxylic acid ethyl ester, $\nu_{max}^{CHCl_3}$ 1,735, 1,605, 1,510, 1,345, 1,125, 1,095 $cm^{-1}$.

The latter compound (24 g) in 400 ml of methanol is mixed with 100 ml of 10% NaOH. The mixture is heated at reflux for 2 hr. The solvent is removed under reduced pressure. The remaining slurry is diluted with water and extracted with ether. The aqueous phase is carefully acidified with dilute HCl and extracted with chloroform. The chloroform extract is dried ($MgSO_4$) filtered, and evaporated to dryness. The residue is crystallized from benzenehexane (1:1) to give the title compound, m.p. 143°.- 144° C, $\nu_{max}^{CHCl_3}$ 2,900 – 2,500, 1,725 – 1,720, 1,600, 1,510 and 1,345 $cm^-$.

In the same manner but replacing N-(2-hydroxyphenyl)-pyrrole with an equivalent amount of N-(5-chloro-2-hydroxyphenyl)-pyrrole, 8-chloro-4-methyl-4H-pyrrolo[2,1-c][1,4]benzoxazine-4-carboxylic acid, m.p. 153° – 154° C (dec), $\nu_{max}^{CHCl_3}$ 1,725, 1,510, 1,330 $cm^{-1}$, is obtained via the intermediate ester, 8-chloro-4-methyl-4H-pyrrolo-[2,1-c][1,4]benzoxazine-4-carboxylic acid ethyl ester, $\nu_{max}^{CHCl_3}$ 1,735 $cm^{-1}$.

In the same manner but replacing p-toluenesulfonic acid with phosphorus pentoxide, hydrochloric acid or polyphosphoric acid, the title compound also is obtained.

The procedures of Examples 2 and 3 are followed to prepare other compounds of formula 3 in which $R^1$, $R^2$, X and n are as defined herein, $R^2$ is hydrogen and A is COOH or $COOR^6$ in which $R^6$ is lower alkyl. Examples of such compounds are listed in Table 1. In each of these examples an equivalent amount of the starting material of formula 2 listed therein is used instead of the starting material of formula 2 described in the procedures of Examples 2 and 3.

TABLE 1

| EX. | STARTING MATERIAL OF FORMULA 2 | | STARTING MATERIAL OF FORMULA $R^3$—CO—$(CH_2)_n$A | | | PRODUCT: (PREFIX LISTED BELOW)-4H-PYRROLO[2,1-c]-[1,4]BENZOXAZINE-4-(SUFFIX LISTED BELOW) |
|---|---|---|---|---|---|---|
| | $R^1$ | $X^1$ | $R^3$ | n | A | Prefix//Suffix |
| 4 | H | OH | $C_2H_5$ | 0 | $COOC_2H_5$ | 4-ethyl//carboxylic acid |
| 5 | H | OH | n-$C_3H_7$ | 1 | $COOCH_3$ | 4-propyl//acetic acid |
| 6 | H | OH | $CH_3$ | 2 | $COOCH_3$ | 4-methyl//propionic acid |
| 7 | 3-$CH_3$ | OH | $C_2H_5$ | 1 | $COOCH_3$ | 4-ethyl-6-methyl//acetic acid |
| 8 | 4-n-$C_3H_7$ | OH | n-$C_3H_7$ | 0 | $COOCH_3$ | 4,7-dipropyl//carboxylic acid |
| 9 | 3-Br | OH | $CH_3$ | 1 | $COOCH_3$ | 6-bromo-4-methyl//acetic acid |
| 10 | 6-Cl | OH | $C_2H_5$ | 2 | $COOCH_3$ | 9-chloro-4-ethyl//propionic acid |
| 11 | 3-$OCH_3$ | OH | n-$C_3H_7$ | 1 | $COOCH_3$ | 6-methoxy-4-propyl//acetic acid |
| 12 | 4-$OC_2H_5$ | OH | $CH_3$ | 0 | $COOCH_3$ | 7-ethoxy-4-methyl//carboxylic acid |
| 13 | 3-$NO_2$ | OH | $C_2H_5$ | 1 | $COOCH_3$ | 4-ethyl-6-nitro//acetic acid |

By following the procedures of Examples 1 to 13 but replacing the starting material of formula 2 ($X^1$ = OH) used therein with the corresponding starting material of formula 2 ($X^1$ = SH, —S—$SO_3$—Na or —S—$SO_3$—K), the corresponding pyrrolobenzothiazine derivative of the product described therein is obtained.

EXAMPLE 14

N,N4-Trimethyl-4H-pyrrolo[2,1-C][1,4]benzoxazine-4-acetamide [3; $R^1$ and $R^2$ = H, $R^3$ = $CH_3$, X = O, n = 1 and A = $CON(CH_3)_2$]

A solution of the acid compound of formula 3, 4-methyl-4H-pyrrolo[2,1-c][1,4]benzoxazine-4-acetic acid (8g), described in Example 2, in 150 ml of dry tetrahydrofuran (THF) is mixed with triethylamine (11g) at −5° C. Ethyl chloroformate (12g) in THF is added and the resultant slurry is agitated for 60 min. Finally, dimethylamine (40% aqueous solution, 250 ml) is added and the reaction mixture is stirred for 18 hr at room temperature. The THF is removed and the residue is distributed between water and chloroform. The chloroform layer is separated and evaporated to dryness. The residue is purified by chromatography using silica gel as the absorbent and chloroform as the eluant. Concentration of the eluate affords the title compound, $\nu_{max}^{CHCl_3}$ 1635, 1510 $cm^{-1}$.

In the same manner but replacing the 40% aqueous solution of dimethylamine with an equivalent amount of the amines of formula $HNR^4R^5$, ammonium hydroxide (concentrated), methylamine (40% aqueous solution), diethylamine (30% aqueous solution), isopropylamine (40% aqueous solution), pyrrolidine (50% aqueous solution), piperidine, morpholine or N-methylpiperazine, 4-methyl-4H-pyrrolo[2,1-c][1,4]benzoxazine-4-acetamide, N,4-dimethyl-4H-pyrrolo[2,1-c][1,4]benzoxazine-4-acetamide, N,N-diethyl-4-methyl-4H-pyrrolo[2,1-c][1,4]benzoxazine-4-acetamide, N-isopropyl-4-methyl-4H-pyrrolo[2,1-c][1,4]benzoxazine-4-acetamide, 1-[(4-methyl-4H-pyrrolo[2,1-c][1,4]benzoxazin-4yl)acetyl]pyrrolidine, 1-[(4-methyl-4H-pyrrolo[2,1-c][1,4]benzoxazin-4-yl)acetyl]piperidine, 4-[(4-methyl-4H-pyrrolo[2,1-c][1,4]benzoxazin-4-yl)acetyl]morpholine, and 1- methyl-4-[(4-methyl-4H-pyrrolo[2,1-c][1,4]benzoxazin-4-yl)acetyl]piperazine, $\nu_{max}{}^{CHCl_3}$ 1640 cm$^{-1}$, are obtained, respectively.

In the same manner but replacing 4-methyl-4H-pyrrolo[2,1-c]-[1,4]benzoxazine-4-acetic acid with an equivalent amount of 8-chloro-4-methyl-4H-pyrrolo[2,1-c][1,4]benzoxazin-4-acetic acid, described in Example 2, 8-chloro-N,N,4-trimethyl-4H-pyrrolo[2,1-c][1,4]benzoxazin-4-acetamide, $\nu_{max}{}^{CHCl_3}$ 1680, 1630, 1510 and 1325 cm$^{-1}$, is obtained.

Likewise, replacement with 4-methyl-8-nitro-4H-pyrrolo-[2,1-c][1,4]benzoxazin-4-acetic acid, described in Example 2, gives N,N,4-trimethyl-8-nitro-4H-pyrrolo[2.1-c][1,4]benzoxazin-4-acetamide.

EXAMPLE 15

N,N,4-Trimethyl-4H-pyrrolo[2,1-c][1,4]benzoxazine-4-carboxamide [3: R$^1$ and R$^2$ = H, R$^3$ = CH$_3$, X = O, n = 0 and A = CON(CH$_3$)$_2$]

A solution of the acid compound of formula 3, 4-methyl-4H-pyrrolo[2,1-c][4,1]benzoxazine-4-carboxylic acid (4.5 g), described in Example 3, is dissolved in dry THF (80 ml) and the solution is treated with triethylamine (6.15 g) at 0° C. Ethyl chloroformate (6.3 g in 25 ml of tetrahydrofuran) is added from a dropping funnel at −5° C and the reaction mixture is stirred for 2 hr. Dimethylamine (130 ml of a 40% aqueous solution) is added and the mixture is allowed to stand overnight at room temperature. Tetrahydrofuran is removed by evaporation under reduced pressure. The residual emulsion is extracted with chloroform. The organic phase is dried (MgSO$_4$) and filtered. The chloroform solution is concentrated and poured through a column of silica gel. Concentration of the eluate affords the title compound, $\nu_{max}{}^{CHCl_3}$ 1640, 1510, 1345 cm$^{-1}$.

In the same manner but replacing the 40% aqueous solution of dimethylamine with an equivalent amount of the amines of formula HNR$^4$R$^5$, ammonium hydroxide (concentrated), methylamine (40% aqueous solution), diethylamine (30% aqueous solution), isopropylamine (40% aqueous solution), piperidine, morpholine or N-methylpiperazine, 4-methyl-4H-pyrrolo[2,1-c][1,4]benzoxazine-4-carboxamide, $\nu_{max}{}^{CHCl_3}$ 3510, 3390, 1675, 1600, 1580 cm$^{-1}$, N,4-dimethyl-4H-pyrrolo[2,1-c][1,4]benzoxazine-4-carboxamide, N,N-diethyl-4-methyl-4H-pyrrolo[2,1-c][1,4]benzoxazine-4-carboxamide, N-isopropyl-4-methyl-4H-pyrrolo[2,1-c][1,4]benzoxazine-4-carboxamide, m.p. 85° − 87° C, $\nu_{max}{}^{CHCl_3}$ 3420, 1675 cm$^{-1}$, 1-[(4-methyl-4H-pyrrolo[2,1-c][1,4]benzoxazin-4-yl)carbonyl]pyrrolidine, 1-[(4-methyl-4H-pyrrolo[2,1-c][1,4]benzoxazin-4-yl)carbonyl]piperidine, 4-[(4-methyl-4H-pyrrolo[2,1-c][1,4]benzoxazin-4-yl)carbonyl]morpholine, and 1-methyl-4-[(4-methyl-4H-pyrrolo[2,1-c][1,4]benzoxazin-4-yl)carbonyl]-piperazine, $\nu_{max}{}^{CHCl_3}$ 1640 cm$^{-1}$, are obtained, respectively.

In the same manner but replacing 4-methyl-4H-pyrrolo[2,1-c]-[1,4]benzoxazine-4-carboxylic acid with an equivalent amount of 8-chloro-4-methyl-4H-pyrrolo[2,1-c][1,4]benzoxazine-4-carboxylic acid, described in Example 3, 8-chloro-N,N,4-trimethyl-4H-pyrrolo[2,1-c]-[1,4]benzoxazine-4-carboxamide, m.p. 118° − 119° C (dec), $\nu_{max}{}^{CHCl_3}$ 1640, 1605, 1510 cm$^{-1}$, is obtained.

Likewise, replacement with 4-methyl-8-nitro-4H-pyrrolo-[2,1-c][1,4]benzoxazine-4-carboxylic acid described in Example 3, gives N,N,4-trimethyl-8-nitro-4H-pyrrolo[2,1-c][1,4]benzoxazine-4-carboxamide.

The procedures of Examples 14 and 15 are followed to prepare other amides of formula 3 in which R$^1$, R$^2$, X and n are as defined herein, R$^2$ is hydrogen and A is CONR$^4$R$^5$ in which R$^4$ and R$^5$ is as defined herein. Examples of such amides are listed in Tables 2 and 3.

In each of these Examples the appropriate starting material of formula 3 (A = COOH) is listed together with the amine used for the preparation of the amide, each starting material being noted by the Example in which it is prepared.

TABLE 2

| EX. | NO. OF EXAMPLE IN WHICH STARTING MATERIAL IS PREPARED | AMINE | PRODUCT: (PREFIX LISTED BELOW)-4H-PYRROLO[2,1-c][1,4]BENZOXAZINE-4-(SUFFIX LISTED BELOW) PREFIX//SUFFIX |
|---|---|---|---|
| 16 | 4 | CH$_3$NH$_2$ | 4-ethyl-N-methyl//carboxamide |
| 17 | 4 | NH$_3$ | 4-ethyl//carboxamide |
| 18 | 5 | (CH$_3$)$_2$NH | N,N-dimethyl-4-propyl//acetamide |
| 19 | 5 | (C$_2$H$_5$)$_2$NH | N,N-diethyl-4-propyl//acetamide |
| 20 | 6 | (n-C$_3$H$_7$)$_2$NH | 4-methyl-N,N-(di-n-propyl)//-propionamide |
| 21 | 6 | CH$_3$NH$_2$ | N,4-dimethyl//propionamide |
| 22 | 7 | NH$_3$ | 4-ethyl-6-methyl//acetamide |
| 23 | 8 | (CH$_3$)$_2$NH | N,N-dimethyl-4,7-dipropyl//-carboxamide |
| 24 | 9 | C$_2$H$_5$NH$_2$ | N-ethyl-6-bromo-4-methyl//-acetamide |
| 25 | 10 | n-C$_3$H$_7$NH$_2$ | 9-chloro-4-ethyl-N-propyl//-propionamide |
| 26 | 11 | n-C$_3$H$_7$NH$_2$ | 6-methoxy-N,4-dipropyl//-acetamide |
| 27 | 12 | (CH$_3$)$_2$NH | 7-ethoxy-N,N,4-trimethyl//-carboxamide |
| 28 | 13 | (C$_2$H$_5$)$_2$NH | N,N,4-triethyl-6-nitro//-acetamide |

TABLE 3

| EX. | NO. OF EXAMPLE IN WHICH STARTING MATERIAL IS PREPARED | AMINE | PRODUCT: (PREFIX LISTED BELOW)-4H-PYRROLO[2,1-c][1,4]BENZOXAZINE-4-(SUFFIX LISTED BELOW) PREFIX//SUFFIX |
|---|---|---|---|
| 29 | 4 | pyrrolidine | 1-[4-ethyl//yl)carbonyl]pyrrolidine |

TABLE 3-continued

| EX. | NO. OF EXAMPLE IN WHICH STARTING MATERIAL IS PREPARED | AMINE | PRODUCT: (PREFIX LISTED BELOW)-4H-PYRROLO[2,1-c][1,4]BENZOXAZINE-4-(SUFFIX LISTED BELOW) PREFIX//SUFFIX |
|---|---|---|---|
| 30 | 4 | piperidine | 1-[(4-ethyl//yl)carbonyl]piperidine |
| 31 | 5 | morpholine | 4[(4-propyl//yl)acetyl]morpholine |
| 32 | 5 | piperazine | 1-[4-propyl//yl)acetyl]piperazine |
| 33 | 6 | N-methyl-piperazine | 1-methyl-4-[(4-methyl//yl)-propionyl]piperazine |
| 34 | 6 | piperazine | 1-[(4-methyl//yl)propionyl]-piperazine |
| 35 | 7 | pyrrolidine | 1-[(4-ethyl-6-methyl//yl)acetyl]-pyrrolidine |
| 36 | 8 | morpholine | 4-[(4,7-dipropyl//yl)carbonyl]-morpholine |
| 37 | 9 | N-ethyl-piperazine | 4-ethyl-1-[(6-bromo-4-methyl//yl)-acetyl]piperazine |
| 38 | 10 | piperidine | 1-[(9-chloro-4-ethyl//yl)pro-pionyl]piperidine |
| 39 | 11 | morpholine | 4-[(6-methoxy-4-propyl//yl)acetyl]-morpholine |
| 40 | 12 | pyrrolidine | 1-[(7-ethoxy-4-methyl//ylcarbonyl]-pyrrolidine |
| 41 | 13 | piperidine | 1-[(4-ethyl-6-nitro//yl)acetyl]-piperidine |

By following the procedure of Examples 14 to 41 but replacing the starting material of formula 3 (X = O and A = COOH) used therein with the corresponding starting material of formula 3 (X = S and A = COOH), the corresponding pyrrolobenzothiazine amide derivative (3; X = S and A = CONR$^4$R$^5$) of the product described therein is obtained.

EXAMPLE 42

4-[2-(Dimethylamino)ethyl]-4-methyl-4H-pyrrolo[2,1-c][1,4]-benzoxazine (1; R$^1$ and R$^2$ = H, R$^3$, R$^4$ and R$^5$ = CH$_3$, X = O and n = 1)

A solution of the amide of formula 3, N,N,4-trimethyl-4H-pyrrolo-[2,1-c][1,4]benzoxazin-4-acetamide (5 g), described in Example 14, in 150 ml of ether is added dropwise to a suspension of lithium aluminum hydride (2.6 g) in anhydrous ether (350 ml). The reaction mixture is stirred at room temperature for 4 hr. Decomposition of the mixture with 11 ml of water gives a white precipitate, which is collected on a filter and washed with ether. The filtrate is extracted with 2% aqueous HCl. The extract is rendered basic with a 10% solution of NaOH and extracted with chloroform. The chloroform extract is dried (MgSO$_4$), filtered and evaporated to give the title compound, nmr (CDCl$_3$) δ 1.61 (s, b 3H), 2.18 (s, 6H), 2.25 (m, 4H), 5.98 (m, 1H), 6.30 (6, J = 3.5 Hz, 1H), 6.9 – 7.5 (m, 5H).

The corresponding hydrochloric acid addition salt (hydrochloride) of the title compound has m.p. 253°–255° C, after recrystallization from isopropanol-ether.

In the same manner but replacing lithium aluminum hydride with an equivalent amount of lithium aluminum hydride-aluminum chloride, aluminum hydride-aluminum chloride, diborane, or sodium borohydride-aluminum chloride, the title compound is also obtained.

In the same manner but replacing N,N,4-trimethyl-4H-pyrrolo-[2,1-c][1,4]benzoxazine-4-acetamide with an equivalent amount of the following amides described in Example 14, 4-methyl-4H-pyrrolo[2,1-c][1,4]benzoxazin-4-acetamide, N,4-dimethyl-4H-pyrrolo[2,1-c][1,4]benzoxazin-4-acetamide, N,N-diethyl-4-methyl-4H-pyrrolo[2,1-c][1,4]benzoxazin-4-acetamide, N-isopropyl-4-methyl-4H-pyrrolo[2,1-c][1,4]benzoxazin-4-acetamide, 1-[(4-methyl-4H-pyrrolo[2,1-c][benzoxazin-4-yl)acetyl]pyrrolidine, 1-[(4-methyl-4H-pyrrolo[2,1-c][1,4]benzoxazin-4-yl)acetyl]piperidine, 4-[(4-methyl-4H-pyrrolo[2,1-c][1,4]benzoxazin-4-yl)acetyl]morpholine, and 1-methyl-4-[(4-methyl-4H-pyrrolo[2,1-c][1,4]benzoxazin-4-yl)acetyl]-piperazine, there are obtained, 4-(2-aminoethyl)-4-methyl-4H-pyrrolo[2,1-c][1,4]benzoxazine, 4-methyl-4-[2-(methylamino)ethyl]-4H-pyrrolo[2,1-c][1,4]benzoxazine, 4-[2-(diethylamino)ethyl]-4-methyl-4H-pyrrolo[2,1-c][1,4]benzoxazine, 4-[2-(isopropylamino)ethyl]-4-methyl-4H-pyrrolo[2,1-c][1,4]benzoxazine, 4-methyl-4-[2-(1-pyrrolidinyl)ethyl]-4H-pyrrolo[2,1-c][1,4]benzoxazine, 4-methyl-4-[2-(piperidino)ethyl]-4H-pyrrolo[2,1-c][1,4]benzoxazine 4-methyl-4-[2-(morpholino)ethyl]-4H-pyrrolo[2,1-c][1,4]benzoxazine, and 4-methyl-4-[2-(4-methyl-1-piperazinyl)ethyl]-4H-pyrrolo[2,1-c][1,4]benzoxazine, nmr (DMSO-d$_6$) δ 1.58 (s, 3H), 2.74 (s, 3H), respectively.

The dihydrochloric acid addition salt of the latter compound, 4-methyl-4-[2-(4-methyl-1-piperazinyl)ethyl]-4H-pyrrolo[2,1-c][1,4]-benzoxazine dihydrochloride, has m.p. 253°–254° C after recrystallization from ethanol-ether.

In the same manner but replacing N,N,4-trimethyl-4H-pyrrolo-[2,1-c][1,4]benzoxazine-4-acetamide with 8-chloro-N,N,4-trimethyl-4H-pyrrolo[2,1-c][1,4]benzoxazine-4-acetamide, described in Example 14, 8-chloro-4-[2-(dimethylamino)ethyl]-4-methyl-4H-pyrrolo[2,1-c][1,4]-benzoxazine is obtained.

Likewise, replacement with N,N,4-trimethyl-8-nitro-4H-pyrrolo[2,1-c][1,4]benzoxazine-4-acetamide gives 4-[2-(dimethylamino)ethyl]-4-methyl-8-nitro-4H-pyrrolo[2,1-c][1,4]benzoxazine.

EXAMPLE 43

4-[(Dimethylamino)methyl]-4-methyl-4H-pyrrolo[2,1-c][1,4]-benzoxazine (1; R$^1$ and R$^2$ = H, R$^3$, R$^4$ and R$^5$ = CH$_3$, X = O and n = O)

A solution of the amide of formula 3, N,N,4-trimethyl-4H-pyrrolo-[2,1-c][1,4]benzoxazine-4-carboxamide (3 g), described in Example 15 in 50 ml of ether is added dropwise to a suspension of lithium aluminum hydride (1.5 g) in anhydrous ether (100 ml) over a period of 30 min. The reaction mixture is stirred at room temperature for 16 hr. Decomposition of the mixture with 6 ml of water gives a white precipitate, which is collected on a filter and washed with ether. The filtrate is extracted with 2% aqueous HCl. The extract is rendered basic with a 10% solution of NaOH and extracted with chloroform. The chloroform extract is dried (MgSO$_4$), filtered and evaporated to give the title compound, nmr (DMSO-d$_6$) δ 1.85 (s, 3H), 2.78 (s, 6H).

The corresponding hydrochloric acid addition salt of the title compound has m.p. 242°–243° C, after recrystallization from ethanol-ether.

In the same manner but replacing lithium aluminum hydride with an equivalent amount of lithium aluminum hydride-aluminum chloride, aluminum hydride-aluminum chloride, diborane or sodium borohydride-aluminum chloride, the title compound is also obtained.

In the same manner but replacing N,N,4-trimethyl-4H-pyrrolo-[2,1-c][1,4]benzoxazine-4-carboxamide with an equivalent amount of the following amides described in Example 15, 4-methyl-4H-pyrrolo[2,1-c][1,4]benzoxazine-4-carboxamide, N,4-dimethyl-4H-pyrrolo[2,1-c][1,4]benzoxazine-4-carboxamide, N,N-diethyl-4-methyl-4H-pyrrolo[2,1-c][1,4]benzoxazine-4-carboxamide, N-isopropyl-4-methyl-4H-pyrrolo[2,1-c][1,4]benzoxazine-4-carboxamide, 1-[(4-methyl-4H-pyrrolo[2,1-c][1,4]benzoxazin-4-yl)carbonyl]pyrrolidine, 1-[(4-methyl-4H-pyrrolo[2,1-c][1,4]benzoxazin-4-yl)carbonyl]piperidine, 4-[(4-methyl-4H-pyrrolo[2,1-c][1,4]benzoxazin-4-yl)carbonyl]morpholine, and 1-methyl-4-[(4-methyl-4H-pyrrolo[2,1-c][1,4]benzoxazin-4-yl)carbonyl]-piperazine, there are obtained, 4-(aminomethyl)-4-methyl-4H-pyrrolo[2,1-c][1,4]benzoxazine, 4-methyl-4-[(methylamino)methyl]-4H-pyrrolo[2,1-c][1,4]benzoxazine, 4-[(diethylamino)methyl]-4-methyl-4H-pyrrolo[2,1-c][1,4-benzoxazine, 4-[(isopropylamino)methyl]-4-methyl-4H-pyrrolo[2,1-c][1,4-benzoxazine, 4-methyl-4-[(1-pyrrolidinyl)methyl]-4H-pyrrolo[2,1-c][1,4]benzoxazine, 4-methyl-4-[(piperidino)methyl]-4H-pyrrolo[2,1-c][1,4]benzoxazine, 4-methyl-4-[(morpholino)methyl]-4H-pyrrolo[2,1-c][1,4]benzoxazine, and 4-methyl-4-[(4-methyl-1-piperazinyl)methyl]-4H-pyrrolo[2,1-c][1,4]-benzoxazine, respectively.

In the same manner but replacing N,N,4-trimethyl-4H-pyrrolo-[2,1-c][1,4]benzoxazine-4-carboxamide with 8-chloro-N,N,4-trimethyl-4H-pyrrolo[2,1-c][1,4]benzoxazine-4-carboxamide, described in Example 15, 8-chloro-4-[(dimethylamino)methyl]-4-methyl-4H-pyrrolo[2,1-c][1,4-benzoxazine, nmr (DMSO-d$_6$) δ 1.87 (s, 3H), 2.73 (broad, 6H), is obtained. The hydrochloric acid addition salt has m.p. 238°–239° C after recrystallization from ethanol-ether.

Likewise, replacement with N,N,4-trimethyl-8-nitro-4H-pyrrolo-[2,1-c][1,4]benzoxazine-4-carboxamide, described in Example 15, gives 4-[(dimethylamino)methyl]-4-methyl-8-nitro-4H-pyrrolo[2,1-c][1,4]-benzoxazine.

By following the procedures of Examples 42 or 43 but using as starting material an equivalent amount of one of the amide compounds of formula 3 described in Examples 16 to 41 the corresponding compounds of formula 1 are obtained. Examples of such compounds of formula 1 are listed as products in Table 4 together with the appropriate starting material. In each case the starting material is noted by the example in which it is prepared.

TABLE 4

| EX. | NO. OF EXAMPLE IN WHICH STARTING MATERIAL IS PREPARED | PRODUCT: (PREFIX LISTED BELOW)-4H-PYRROLO[2,1-c][1,4]BENZOXAZINE |
|---|---|---|
| 44 | 16 | 4-ethyl-4-(methylaminomethyl) |
| 45 | 17 | 4-(aminomethyl)-4-ethyl |
| 46 | 18 | 4-[2-(dimethylamino)ethyl]-4-propyl |
| 47 | 19 | 4-[2-(diethylamino)ethyl]-4-propyl |
| 48 | 20 | 4-[3-(di-n-propylamino)propyl]-4-methyl |
| 49 | 21 | 4-methyl-4-[3-(methylamino)propyl] |
| 50 | 22 | 4-(2-aminoethyl)-4-ethyl-6-methyl |
| 51 | 23 | 4-(dimethylaminoethyl)-4,7-dipropyl |
| 52 | 24 | 6-bromo-4-[2-(ethylamino)ethyl]-4-methyl |
| 53 | 25 | 9-chloro-4-ethyl-4-[3-(propylamino)propyl] |
| 54 | 26 | 6-methoxy-4-propyl-4-[2-(propylamino)ethyl] |
| 55 | 27 | 4-(dimethylaminomethyl)-7-ethoxy-4-methyl |
| 56 | 28 | 4-[2-(dimethylamino)ethyl]-4-ethyl-6-nitro |
| 57 | 29 | 4-ethyl-4-[(1-pyrrolidinyl)methyl] |
| 58 | 30 | 4-ethyl-4-(piperidinomethyl) |
| 59 | 31 | 4-[2-(morpholino)ethyl]-4-propyl |
| 60 | 32 | 4-[2-(1-piperazinyl)ethyl]-4-propyl |
| 61 | 33 | 4-methyl-4-[3-(4-methyl-1-piperazinyl)propyl] |
| 62 | 34 | 4-methyl-4-[3-(1-piperazinyl)propyl] |
| 63 | 35 | 4-ethyl-6-methyl-4-[2-(1-pyrrolidinyl)ethyl] |
| 64 | 36 | 4,7-dipropyl-4-(morpholinomethyl) |
| 65 | 37 | 6-bromo-4-ethyl-4-[2-(4-ethyl-1-piperazinyl)ethyl] |
| 66 | 38 | 9-chloro-4-ethyl-4-[3-(piperidino)propyl] |
| 67 | 39 | 6-methoxy-4-[2-(morpholino)ethyl]-4-propyl |
| 68 | 40 | 7-ethoxy-4-methyl-4-[(1-pyrrolidinyl)methyl] |
| 69 | 41 | 4-ethyl-6-nitro-4-[2-(piperidino)ethyl] |

By following the procedure of Examples 42 to 69 but replacing the starting material of formula 3 (X = O and A = CONR$^4$R$^5$) used therein with the corresponding starting material of formula 3 (X = S and A = CONR$^4$R$^5$), the corresponding pyrrolobenzothiazine derivative of formula 1 of the product described therein is obtained.

EXAMPLE 70

N,N,4-Trimethyl-4H-pyrrolo[2,1-c][1,4]benzoxazine-4-carboxamide

A mixture of 1-(o-hydroxyphenyl)pyrrole (500 mg), N,N-dimethyl-pyruvamide (580 mg), described by W. F. Gresham in U.S. Pat. No. 2,429,877, issued Oct. 28, 1947, 1.7 g of phosphorus pentoxide, 0.5 g of diatomaceous earth (Celite) in 75 ml of benzene is stirred at room temperature for 15 min. and then at 70° C for 1½ hr. The reaction mixture is filtered. The filtrate is washed with water, dried (MgSO$_4$) and concentrated to give the title compound, identical to the product of Example 15.

In the same manner but using an equivalent amount of the appropriate starting material of formula 2 together with the appropriate α-, β- γ- or δ-ketoamide, the products listed in Examples 14 to 43 are obtained. For example, according to the present procedure 1-(o-hydroxyphenyl)pyrrole condenses with acetoacetamine to give 4-methyl-4H-pyrrolo[2,1-c][1,4]benzoxazine-4-acetamide, identical to the amide described in Example 14.

EXAMPLE 71

4-(Hydroxymethyl)-4-methyl-4H-pyrrolo[2,1-c][1,4]benzoxazine (3: R$^1$ and R$^2$ = H, R$^3$ = CH$_3$, X = O, n = O and A = CH$_2$OH)

A mixture of 1-(o-hydroxyphenyl)pyrrole (477 mg), acetoxyacetone (348 mg), p-toluenesulfonic acid (50 mg), and benzene (60 ml) is heated at reflux with a water-separator for 2 hr. An additional portion of acetoxyacetone (174 mg) is added and the reaction mixture is kept under the refluxing conditions for an additional 16 hr. After cooling, the benzene solution is washed with 10% solution of NaHCO$_3$ and evaporated. The residue is dissolved in methanol (50 ml) and 1 ml of 50% solution of KOH is added. The resultant solution is kept at room temperature for 12 hr. The methanol is removed under reduced pressure. The residue is partitioned between water and chloroform. The organic phase is separated, concentrated and filtered through a column of silica to give the title compound, $\nu_{max}^{CHCl_3}$ 3575, 1600, 1510, 1345, 1110, 1080, 1035 cm$^{-1}$.

EXAMPLE 72

4-[2-(Dimethylamino)methyl]-4-methyl-4H-pyrrolo[2,1-c][1,4]benzoxazine 4-(Hydroxymethyl)-4-methyl-4H-pyrrolo[2,1-c][1,4]benzoxazine (9 g), described in Example 71, is dissolved in dry pyridine (20 ml). p-Toluenesulfonyl chloride (7.4 g) is added portionwise to the vigorously stirred and cooled solution. The mixture is stirred further at 0° C for 1 hr, ice and water is then added and the aqueous mixture is extracted with ether. The combined ether extracts are washed with 10% ice-cold hydrochloric acid, water, 5% sodium bicarbonate water and dried (Na$_2$SO$_4$). Concentration of the extracts affords the corresponding tosylate.

A mixture of the latter compound (11.7 g) in 100 ml THF and 40% aqueous dimethylamine (199 ml) is heated at reflux for 16 hr. Most of the tetrahydrofuran is removed under reduced pressure. The milky water solution is extracted with ether and washed with water until the water tests neutral. The extract is dried (Na$_2$SO$_4$) and evaporated to yield the title compound, identical to the product of Example 43.

By following the procedure of Examples 71 and 72 in sequence but using as starting material in Example 71 an appropriate starting material of formula 2, and appropriate ketoalcohol lower alkyl ester of formula R$^3$CO(CH$_2$)$_n$-A in which R$^3$ and n are as described above and A is CH$_2$OCOR$^7$ in which R$^7$ is as described above; followed by the use of an appropriate amine of formula HNR$^4$R$^5$, for for example the amines described in Example 14, in the procedure of Example 72, the respective compound of formula 1, for example those described in Examples 42 to 69, are obtained.

EXAMPLE 73

N-Acetyl-4-(aminomethyl)-4-methyl-4H-pyrrolo[2,1-c][1,4]benzoxazine (3: R$^1$ and R$^2$ = H, R$^3$ = CH$_3$, X = O, n = 0 and A = CH$_2$NHCOCH$_3$)

Acetamidoacetone (460 mg), described by J. D. Hepworth, Org. Syn., 45, 1 (1965), 1-(o-hydroxyphenyl)pyrrole (636 mg), and p-toluenesulfonic acid (70 mg) is dissolved in toluene (100 ml). The solution is heated to reflux under a water-separator for 2 hr. After cooling the reaction mixture is washed with 5% NaHCO$_3$, water, and saturated brine solution. The organic phase is dried (MgSO$_4$), filtered and evaporated to yield the title compound, nmr (DMSO-d$_6$) δ 1.48 (s, 3H), 1.78 (s, 3H), 3.42 (d, J = 6Hz, 2H), 6.06 (2 Xd, J = 3.5 Hz, J$_2$ = 1.5Hz 1H), 6.25 (t, J, = 3.5Hz, 1H), 7.05 and 7.47 (m, 5H), 7.58 (broad, 1H).

Reduction of the title compound with lithium aluminum hydride according to the procedure of Example 42 gives the compound of formula 1, 4-[2-(ethylamino)ethyl]-4-methyl-4H-pyrrolo[2,1-c][1,4]benzoxazine.

By following the procedure of Example 73, but using as starting material an equivalent amount of the appropriate starting material of formula 2, for example, those described in Examples 3 to 13 and using an equivalent amount of an appropriate ketoamide of formula

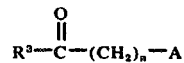

in which R$^3$ and n are as defined above and A is CH$_2$NR$^4$COR$^8$ wherein R$^4$ and R$^8$ are as described above, the corresponding secondary amine compounds of formula 1 are obtained.

EXAMPLE 74

4-[2-(Dimethylamino)ethyl]-4-methyl-4H-pyrrolo[2,1-c][1,4-benzoxazine

To a solution of 1-dimethylamino-3-butanone (1.0 g) dissolved in toluene (10 ml), p-toluenesulfonic acid (1.3 g) is added. The suspension is stirred for 10 min. 1-(o-Hydroxyphenyl)pyrrole (1.0 g) in toluene (5 ml) is added to the suspension and the resulting solution stirred for 2 hr. Additional p-toluenesulfonic acid (0.5 g), is added together with ca. 0.5 g of hydrated alkali-aluminum silicate. The mixture is heated at 80° C for 30 min. The mixture is cooled and diluted with water. The organic layer is separated and the aqueous layer extracted with toluene. The organic layers are washed with water. The combined aqueous phase is rendered alkaline with conc NH$_4$OH and extracted with toluene. The latter extract is treated with charcoal and then concentrated to afford the title compound, identical to the compound of the same name described in Example 42.

By following the procedure of Example 74, but using as starting material an equivalent amount of the appropriate starting material of formula 2, for example, those described in Examples 2 to 13 and using an equivalent amount of the appropriate aminoketone of formula R$^3$CO-(CH$_2$)$_n$-A wherein R$^3$, n and A are as defined herein, the corresponding compounds of formula, 1 are obtained.

EXAMPLE 75

1-Chloro-4-[(dimethylamino)methyl]-4-methyl-4H-pyrrolo[2,1-c][1,4]-benzoxazine (1: $R^1 = H$, $R^2 = 8$-Cl, $R^3$, $R^4$ and $R^5 = CH_3$, X = O and n = 1)

A solution of 4-[(dimethylamino)methyl]-4-methyl-4H-pyrrolo-[2,1-c][1,4]benzoxazine hydrochloride (4.5 g), described in Example 42, in 200 ml of chloroform is treated with a solution of sulphuryl chloride (2.2 g) in 100 ml of chloroform and the inside temperature is kept at 0° C. The reaction mixture is stirred for 2 hr without cooling, evaporated to dryness, and the solid residue crystallized repeatedly from methylene chloride-ether to give the title compound in the form of its hydrochloric acid addition salt, m.p. 212° – 214° C.

The title compound in the form of its free base is obtained by decomposing the aforementioned salt. For example, a chloroform solution of the salt is washed with 5% $Na_2CO_3$ solution and brine and evaporated to dryness to give the title compound, nmr ($CDCl_3$) δ 2.02 (s, 3H), 2.95 (m, 6H), 3.48 (m, 2H), 6.28 (s, 2H), 7.20 (m, 3H).

By following the procedure of Example 75 but using as a starting material the appropriate starting material of formula 3, for example those described in Examples 2 to 41 or the appropriate starting material of formula 1, for example, those described in Examples 42 to 69, together with the appropriate nucleophilic reagent, for instance, sulfuryl chloride or bromide, respective compounds of formulae 3 and 1 in which $R^2$ is halogen are obtained. More specifically exemplified, the use of 4-methyl-8-nitro-4H-pyrrolo-[2,1-c][1,4]benzoxazine-4-acetic acid methyl ester, described in Example 2 gives 1-chloro-4-methyl-8-nitro-4H-pyrrolo[2,1-c][1,4]-benzoxazine-4-acetic acid methyl ester, m.p. 124° – 125° C.

EXAMPLE 76

4-[(Dimethylamino)methyl]-4-methyl-8-nitro-4H-pyrrolo[2,1-c][1,4]-benzoxazine (1; $R^1 = H$, $R^2 = 8$-$NO_2$, $R^3$, $R^4$ and $R^5 = CH_3$, X = O and n = 1)

A cold mixture of 90% nitric acid (8.3 g) and acetic anhydride (50 ml) is added dropwise to a solution of 4-[(dimethylamino)methyl]-4-methyl-4H-pyrrolo[2,1-c][1,4]benzoxazine (3 g), described in Example 42, in acetic anhydride (50 ml) at −50° C. The addition is completed within 50 min. The reaction mixture is stirred at −50° C for 1 hr, and then allowed to reach the ambient temperature. After being poured on 1800 g of ice-water, the mixture is neutralized with solid sodium carbonate and extracted with ether. The organic phase is washed with water, dried ($MgSO_4$), filtered and evaporated to dryness. The residue is dissolved in chloroform, acidified with ethereal HCl and the solvents are removed under reduced pressure. The residue is recrystallized from ethanol-ether to give the title compound in the form of its hydrochloric acid addition salt, m.p. 247° – 248° C.

Decomposition of the latter salt to its corresponding free base in the manner described in Example 75, gives the title compound $\delta_{max}^{nujol}$ 1,520, 1,490, 1,465 cm$^{-1}$.

By following the procedure of Example 76 but using as a starting material the appropriate starting material of formula 3, for example those described in Examples 2 to 41 or the appropriate starting material of formula 1, for example those described in Examples 42 to 69, the corresponding compounds of formula 3 and 1 in which $R^2$ is nitro are obtained.

EXAMPLE 77

1-Trifluoroacetyl-N,N,4-trimethyl-4H-pyrrolo[2,1-c][1,4]benzoxazine-4-acetamide [3: $R^1 = H$, $R^2 = $ 1-$COCF_3$, $R^3 = CH_3$, X = O, n = 1 and A = $CON(CH_3)_2$]

N,N,4-Trimethyl-4H-pyrrolo[2,1-c][1,4]-benzoxazine-4-acetamide (1.0 g) described in Example 14, is dissolved in 80 ml of dry benzene and treated with a solution of trifluoroacetic anhydride (0.84 g) in 20 ml of the same solvent. The reaction mixture is stirred at room temperature for 3 hr and then heated to reflux for 30 min. The cold benzene solution is washed successively with water, 10% aq. $NaHCO_3$ and again with water. Removal of the solvent affords an oily product which is purified by chromatography (silica gel-chloroform) to give the title compound as a solid, m.p. 81° – 83° C.

By following the procedure of Example 77 but using as a starting material the appropriate starting material of formula 3, for example those described in Examples 2 to 41 or the appropriate starting material of formula 1, for example those described in Examples 42 to 69, together with the appropriate nucleophilic reagent, for instance, acetic anhydride or trifluoroacetic anhydride, the corresponding compounds of formulae 3 and 1 in which $R^2$ is lower alkanoyl or trifluoroacetyl are obtained.

EXAMPLE 78

4,4-Dimethyl-4H-pyrrolo[2,1-c][1,4]benzoxazine (5; $R^1 = H$, $R^3$ and $R^9 = CH_3$ and X = O)

p-Toluenesulfonic acid monohydrate (110 mg) is dissolved in 70 ml of dry benzene and the solution heated at reflux with a water-separator for about 10 minutes. A solution of 1-(o-hydroxyphenyl)-pyrrole (1.1 g) in dry benzene (80 ml) is added, followed by 10 ml of acetone. The reaction mixture is heated at reflux with the water-separator for 15 hr, cooled, and washed with a solution of $NaHCO_3$. The benzene solution is evaporated to dryness. The residue is subjected to chromatography on silica gel, using chloroform as eluent. Evaporation of the first portion of the eluate gives the title compound, m.p. 38° – '° C, $\nu_{max}^{CHCl_3}$ 1600, 1510, 1345 cm$^{-1}$.

Continued elution gives a dimer of formula 6 in which $R^1$ is H and $R^3$ and $R^9$ are methyl, 1,1'-isopropylidene-bis-(4,4-diemthyl-4H-pyrrolo[2,1-c][1,4]benzoxazine), m.p. 141°–143° C after recrystallization from ether-hexane.

By following the procedure of Example 78, but using as starting material the appropriate compound of formula 2, for example those described in Examples 3 to 13, and using the appropriate ketone of formula $R^3$-CO-$R^9$ as defined herein, other compounds of formula 5 are obtained. For example the use of 1-(5-chloro-2-hydroxyphenyl)pyrrole, described in Example 1, gives 8-chloro-4,4-dimethyl-4H-pyrrole[2,1-c][1,4]benzoxazine, m.p. 75° – 78° C. During the latter preparation the corresponding dimer, 1,1'-isopropylidene-bis-(8-chloro-4,4-dimethyl-4H-pyrrolo[2,1-c][1,4]benzoxazine), m.p. 170° – 173° C, is obtained.

EXAMPLE 79

1-[(Dimethylamino)methyl]-4,4-dimethyl-4H-pyrrolo[2,1-c][1,4]benzoxazine (4; $R^1 = H$, $R^3$, $R^4$, $R^5$ and $R^9 = CH_3$ and $X = O$)

A mixture of 18 ml of 40% aqueous dimethylamine solution and 19.8 ml of acetic acid is treated with 9 ml of 37% formalin at 10° – 15° C. The resulting solution is added at once to 10 g of 4,4-dimethyl-4H-pyrrolo[2,1-c][1,4]benzoxazine (10. g, described in Example 78) in 30 ml of ethanol. The reaction mixture is stirred at ambient temperature for 18 hr. Ethanol is removed under reduced pressure, and the remaining oily suspension is extracted with chloroform. The combined extracts are dried ($Na_2SO_4$), filtered, and evaporated to yield the title compound, nmr ($CDCl_3$) δ 1.56 (s, 6H), 2.67 (d, J = 4.5Hz, 6H), 4.70 (d, J = 4.5Hz, 2H), 6.08 and 6.85 (d, 2H), 6.95 – 7.70 (m, 4H), 12.4 (broad, 1H).

The title compound is dissolved in anhydrous ether and acidified with ethereal HCl. The precipitate is collected to give the hydrochloric acid addition salt (hydrochloride) of the title compound, m.p. 188° – 189° C after recrystallization from ethanol ether.

By following the procedure of this example but using as starting materials the appropriate base of formula $HNR^4R^5$ described above and the appropriate starting material of formula 5 then other compounds of formula 4 are obtained. For example, the use of morpholine with 4,4-dimethyl-4H-pyrrolo[2,1-c][1,4]benzoxazine, described in Example 78, gives 4,4-dimethyl-1-(morpholinomethyl)-4H-pyrrolo[2,1-c][1,4]benzoxazine, m.p. 150° – 151° C. The corresponding maleic acid addition salt (maleate) of the latter compound has m.p. 149° – 150° C.

Alternatively, the procedure of this Example is followed to prepare compounds of formula 3 in which $R^2$ is $CH_2NR^4R^5$ in which $R^4$ and $R^5$ are as defined herein and A is $COOR^6$ or $CONR^4R^5$ in which $R^4$, $R^5$ or $R^6$ are as defined herein. For example, by using dimethylamine (40% aqueous solution) as the base and N-isopropyl-4-methyl-4H-pyrrolo[2,1-c][1,4]benzoxazine-4-carboxamide, described in Example 15, 1-[(dimethylamino)methyl]-N-isopropyl-4-methyl-4H-pyrrolo-2,1-c][1,4]benzoxazine-4-carboxamide, nmr ($CDCl_3$) δ 1.02 and 1.16 (2 xd, J = 7Hz, 6H), 1.75 (s, 3H), 2.70 (d, J = 4Hz, 6H), is obtained. [The corresponding hydrochloric acid addition salt of the latter compound has m.p. 125° – 127° C). Reduction of the latter compound according to the procedure of Example 42 yields 1-[(dimethylamino)-methyl]-4-[(isopropylamino)methyl]-4-methyl-4H-pyrrolo[2,1-c][1,4]-benzoxazine.

We claim:

1. A compound of the formula 1

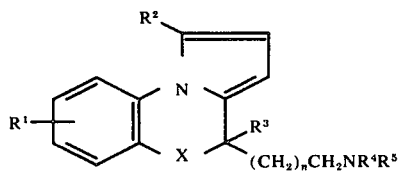

in which $R^1$ is hydrogen, lower alkyl, halogen, lower alkoxy or nitro; $R^2$ is hydrogen, halogen, nitro, lower alkanoyl, trifluoroacetyl or $CH_2NR^4R^5$ in which $R^4$ and $R^5$ are the same or different selected from the group consisting of hydrogen and lower alkyl, or $R^4$ and $R^5$ together with the nitrogen atom to which they are joined from a heterocyclic amine radical selected from the group consisting of 1-pyrrolidinyl, piperidino, morpholino, 1-piperazinyl and 4-(lower alkyl)-1-piperazinyl; $R^3$ is lower alkyl; $R^4$ and $R^5$ are as defined herein; X is oxy or thio; and n is an integer from zero to two; and the acid addition salts thereof with pharmaceutically acceptable acids.

2. 4-[2-(Dimethylamino)ethyl]-4-methyl-4-H-pyrrolo[2,1-c]-[1,4]benzoxazine, as claimed in claim 1.

3. 4-[2-(Dimethylamino)ethyl]-4-methyl-4H-pyrrolo[2,1-c]-[1,4]benzoxazine hydrochloride, as claimed in claim 1.

4. 4-Methyl-4-[2-(4-methyl-1-piperazinyl)ethyl]-4H-pyrrolo-[2,1-c][1,4]benzoxazine, as claimed in claim 1.

5. 4-Methyl-4-[2-(4-methyl-1-piperazinyl)ethyl]-4H-pyrrolo-[2,1-c][1,4]benzoxazine dihydrochloride, as claimed in claim 1.

6. 4-[(Dimethylamino)methyl]-4-methyl-4H-pyrrolo-[2,1-c][1,4]benzoxazine, as claimed in claim 1.

7. 4-[(Dimethylamino)methyl]-4-methyl-4H-pyrrolo-[2,1-c][1,4]benzoxazine hydrochloride, as claimed in claim 1.

8. 8-Chloro-4-[(dimethylamino)methyl]-4-methyl-4H-pyrrolo-[2,1-c][1,4]benzoxazine, as claimed in claim 1.

9. 8-Chloro-4-[(dimethylamino)methyl]-4-methyl-4H-pyrrolo-[2,1-c][1,4]benzoxazine hydrochloride, as claimed in claim 1.

10. 1-Chloro-4-[(dimethylamino)methyl]-4-methyl-4H-pyrrolo-[2,1-c][1,4]benzoxazine, as claimed in claim 1.

11. 1-Chloro-4-[(dimethylamino)methyl]-4-methyl-4H-pyrrolo-[2,1-c][1,4]benzoxazine hydrochloride, as claimed in claim 1.

12. 4-[(Dimethylamino)methyl]-4-methyl-8-nitro-4H-pyrrolo-[2,1-c][1,4]benzoxazine, as claimed in claim 1.

13. 4-[(Dimethylamino)methyl]-4-methyl-8-nitro-4H-pyrrolo-[2,1-c][1,4]benzoxazine hydrochloride as claimed in claim 1.

14. The compound of formula 1 of claim 1 in which $R^1$ is hydrogen or chlorine; $R^2$ is hydrogen or chlorine; $R^3$ is lower alkyl; $R^4$ and $R^5$ each are lower alkyl or $R^4$ and $R^5$ together with the nitrogen to which they are joined form a heterocyclic amine radical selected from the group consisting of 1-pyrrolidinyl, piperidino, morpholino, 1-piperazinyl and 4-(lower alkyl)-1-piperazinyl; X is oxy; and n is an integer from zero to two.

15. The compound of claim 14 in which n is zero or one.

16. A compound of the formula 4

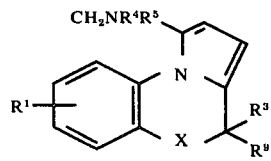

in which $R^1$ is hydrogen, lower alkyl, halogen, lower alkoxy or nitro; $R^3$ is lower alkyl, $R^4$ and $R^5$ are the same or different selected from the group consisting of hydrogen and lower alkyl, or $R^4$ and $R^5$ together with the nitrogen atom to which they are joined form a heterocyclic amine selected from the group consisting of 1-pyrrolidinyl, piperidino, morpholino, 1-piperazinyl and 4-(lower alkyl)-1-piperazinyl; $R^9$ is lower alkyl and X is oxy or thio; and the acid addition salts thereof with pharmaceutically acceptable acids.

17. 1-[(Dimethylamino)methyl]-4,4-dimethyl-4H-pyrrolo-[2,1-c][1,4]benzoxazine, as claimed in claim 16.

18. 1-[(Dimethylamino)methyl]-4,4-dimethyl-4H-pyrrolo-[2,1-c][1,4]benzoxazine hydrochloride, as claimed in claim 16.

19. 4,4-Dimethyl-1-(morpholinomethyl)-4H-pyrrolo[2,1-c]-[1,4]benzoxazine, as claimed in claim 16.

20. 4,4-Dimethyl-1-(morpholinomethyl)-4H-pyrrolo[2,1-c]-[1,4]benzoxazine maleate, as claimed in claim 16.

21. The compound of claim 16 in which $R^1$ is hydrogen or chlorine; $R^3$ is lower alkyl; $R^4$ and $R^5$ each are lower alkyl or together with the nitrogen to which they are joined form a heterocyclic amine radical selected from the group consisting of 1-pyrrolidinyl, piperidino, morpholino, 1-piperazinyl and 4-(lower alkyl)-1-piperazinyl; $R^9$ is lower alkyl and X is oxygen.

22. A compound of the formula 3

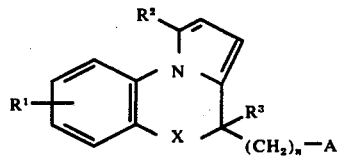

in which $R^1$ is hydrogen, lower alkyl, halogen, lower alkoxy or nitro; $R^2$ is hydrogen, halogen, nitro, lower alkanoyl, trifluoroacetyl or $CH_2NR^4R^5$ in which $R^4$ and $R^5$ are the same or different selected from the group consisting of hydrogen and lower alkyl, or $R^4$ and $R^5$ together with the nitrogen atom to which they are joined form a heterocyclic amine radical selected from the group consisting of 1-pyrrolidinyl, piperidino, morpholino, 1-piperazinyl and 4-(lower alkyl)-1-piperazinyl; $R^3$ is lower alkyl; X is oxy or thio; n is an integer from zero to two; and A is selected from the group consisting of $COOR^6$ in which $R^6$ is hydrogen or lower alkyl, $CONR^4R^5$ in which $R^4$ and $R^5$ are as defined herein, $CH_2OCOR^7$ in which $R^7$ is lower alkyl, or $CH_2NR^4COR^8$ in which $R^4$ is as defined herein and $R^8$ is an alkyl containing one to five carbon atoms.

23. A compound of formula 5

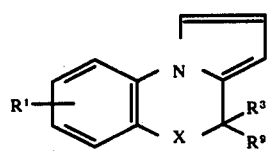

in which $R^1$ is hydrogen, lower alkyl, halogen, lower alkoxy or nitro; $R^3$ is lower alkyl; $R^9$ is lower alkyl; and X is oxy or thio.

24. The process for preparing a compound of claim 1, comprising:
condensing a compound of the formula 2

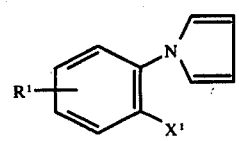

in which $R^1$ is as defined therein and $X^1$ is hydroxy, mercapto, $-S-SO_3-Na$ or $-S-So_3-K$ with a compound of formula

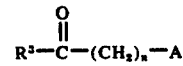

wherein $R^3$ is lower alkyl, n is an integer from zero to two and A is $COOR^6$ in which $R^6$ is hydrogen or lower alkyl, in the presence of a Friedel-Crafts type catalyst to obtain the corresponding compound of formula 3

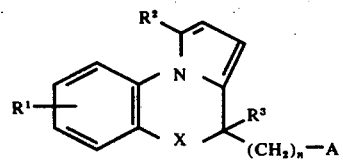

in which $R^1$, $R^3$, n and A are defined hereinabove, X is oxy or thio and $R^2$ is hydrogen; subjecting said compound of formula 3 to hydrolysis to the corresponding acid in the case where $R^6$ is lower alkyl; subjecting the acid compound to amidation with an appropriate amine for formula $NHR^4R^5$ in which $R^4$ and $R^5$ are as defined in claim 1 to give the amide and reducing the amide with a suitable complex metal hydride to give the corresponding compound of formula 1, wherein the compound having the formula

is added to a mixture of the compound of formula 2 and the Friedel-Crafts type catalyst.

25. A process for preparing a compound of formula 4 of claim 16, comprising:
reacting from 10 minutes to 60 hours at temperatures ranging from 20° C to 160° C a compound of formula 2.

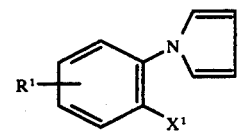

in which $R^1$ is as defined in claim 15 and $X^1$ is hydroxy, mercapto, $-S-SO_3-Na$ or $-S-SO_3-K$ with a ketone of formula

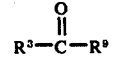

in which $R^3$ and $R^9$ are as described in claim 15, in the presence of 0.01 to 100 molar equivalents of a Friedel-Crafts type catalyst to obtain the corresponding compound of formula 5

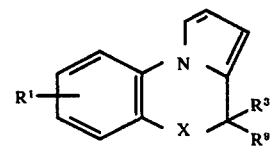

in which $R^1$, $R^3$ and $R^9$ are as defined herein, and X is oxy or thio and reacting the last-named compound with formaldehyde and an amine of formula $NHR^4R^5$ in which $R^5$ are as described in claim 15 to obtain the corresponding compound of formula 4 of claim 15.

26. The process of claim 25 wherein said compound of formula 4 is reacted with a pharmaceutically acceptable acid to obtain the corresponding acid addition salt.

27. A method of treating hypertension in warm-blooded animals, comprising: administering to said animals an effective antihypertensive amount of the compound of formula 1 of claim 1.

28. A method of treating hypertension in warm-blooded animals, comprising: administering to said animals an effective antihypertensive amount of the compound of formula 4 of claim 16.

29. A method of depressing the central nervous system of warm-blooded animals, comprising: administering to said animals an effective central nervous system depressing amount of the compound of formula 1 of claim 1.

30. A method of depressing the central nervous system of warm-blooded animals, comprising: administering to said animals on effective central nervous system depressing amount of the compound of formula 4 of claim 16.

* * * * *